United States Patent
Anklesaria

(10) Patent No.: US 9,140,658 B1
(45) Date of Patent: Sep. 22, 2015

(54) FLUID DETECTION DEVICE

(71) Applicant: Kaiomars P. Anklesaria, Bloomingdale, GA (US)

(72) Inventor: Kaiomars P. Anklesaria, Bloomingdale, GA (US)

(73) Assignee: Enuresis Solutions LLC, Savannah, GA (US)

(*) Notice: Subject to any disclaimer, the term of this patent is extended or adjusted under 35 U.S.C. 154(b) by 324 days.

(21) Appl. No.: 13/674,554

(22) Filed: Nov. 12, 2012

Related U.S. Application Data

(63) Continuation of application No. 13/344,823, filed on Jan. 6, 2012.

(51) Int. Cl.
| | |
|---|---|
| *G01R 27/08* | (2006.01) |
| *G01N 27/04* | (2006.01) |
| *G01N 27/48* | (2006.01) |
| *A61F 13/42* | (2006.01) |

(52) U.S. Cl.
CPC ............. *G01N 27/04* (2013.01); *G01N 27/48* (2013.01); *A61F 13/42* (2013.01)

(58) Field of Classification Search
None
See application file for complete search history.

(56) References Cited

U.S. PATENT DOCUMENTS

| | | | |
|---|---|---|---|
| 4,506,540 A * | 3/1985 | Marsh ........................ | 73/29.05 |
| 4,539,559 A * | 9/1985 | Kelly et al. ................ | 340/573.5 |
| 2002/0192829 A1* | 12/2002 | Zainiev et al. .................. | 436/39 |
| 2003/0011482 A1* | 1/2003 | Harms et al. .................. | 340/605 |
| 2006/0216813 A1* | 9/2006 | Gumbrecht et al. ........ | 435/287.2 |
| 2007/0259469 A1* | 11/2007 | Santagato ...................... | 438/49 |
| 2008/0036444 A1* | 2/2008 | Paulus et al. ................. | 324/71.1 |
| 2013/0245388 A1* | 9/2013 | Rafferty et al. ............... | 600/301 |

* cited by examiner

*Primary Examiner* — Minh N Tang
(74) *Attorney, Agent, or Firm* — G. Brian Pingel; David M. Breiner

(57) ABSTRACT

Provided is a fluid detection device. The fluid detection device may be used to detect body fluids, for example, blood or urine. The fluid detection device includes a first conductive member on a first side of a non-conductive member which is fluid absorbent, and a second conductive member on a second side of the non-conductive member, wherein the first and second conductive members are arranged across a thickness of the non-conductive member. A voltage is applied across the two conducting members. When body fluid is absorbed by the non-conductive member, its resistance decreases so that measurable current flows between the conducting members and can be sensed and used for alarm or other purposes.

2 Claims, 17 Drawing Sheets

FLUID DETECTION DEVICE

CROSS-REFERENCE TO RELATED APPLICATION

This application is a continuation-in-part (CIP) of U.S. application Ser. No. 13/344,823 filed with the United States Patent and Trademark Application (USPTO) on Jan. 6, 2012, the entire contents of which is incorporated herein by reference.

BACKGROUND

1. Field

Example embodiments relate to a fluid detection device and more particularly to a fluid detection device configured to detect body fluids on the surface of the body or outside the body 2. Description of the Related Art In modern day medicine and everyday life, it is relatively common for patients to experience the involuntary loss of body fluids. Simple examples may be involuntary urination by children or adults (usually a non life threatening matter), and blood loss due to seepage through an incision, whether surgically created, or temporarily created for inserting a tube for dialysis (this loss of fluid can be life threatening). Several devices are available to monitor a patient's blood loss. These devices, however, may be difficult to manufacture and use, and consequently expensive. Thus, an improved and more economical blood leakage monitoring device is desired.

SUMMARY

Example embodiments are directed to a pliable fluid detection device configured to detect body fluid, for example, blood or urine. The fluid detection device may be attached directly to a person, a bandage, or an article of clothing, all extraneous to the body's surface or skin.

In accordance with example embodiments, a fluid detection device may include a first electrically conductive member, or electrode, on a first side of an electrically non-conductive member, or insulator, and a second electrically conductive member, or electrode, on a second side of the non-conductive member, wherein the first and second conductive members are arranged across a narrow thickness of the non-conductive member. A small voltage, typically from a battery, is applied across the electrodes. The non-conductive member would be fluid absorbent, and absorb body fluids such as urine or blood. Upon absorbing body fluid, this non-conductive member's electrical resistance becomes less, until at some point electric current will flow between the electrodes. This current can be sensed and measured and would be indicative of the presence of unwanted body fluid.

BRIEF DESCRIPTION OF THE DRAWINGS

Example embodiments are described in detail below with reference to the attached drawing figures, wherein.

DETAILED DESCRIPTION

Figure 1:
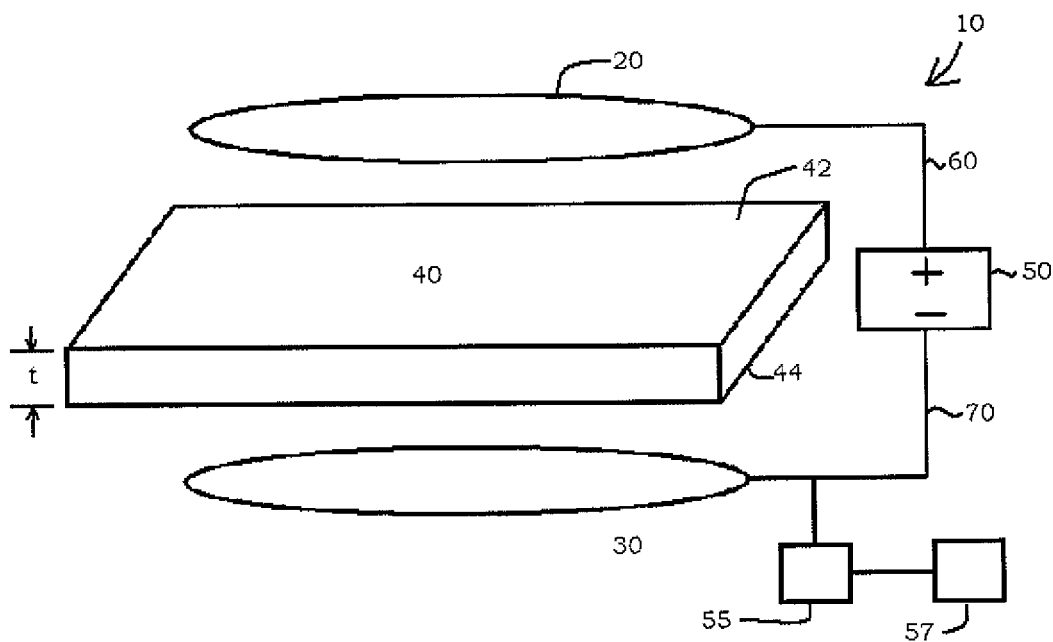
FIG. 1 is an exploded view of a fluid detection device in accordance with example embodiments.

Example embodiments of the invention will now be described with reference to the accompanying drawings.

Example embodiments, however, should not be construed as limiting the invention since the invention may be embodied in different forms. Example embodiments illustrated in the figures are provided so that this disclosure will be thorough and complete. In the drawings, the sizes of components may be exaggerated for clarity.

In this application, when an element is referred to as being "on," "attached to," "connected to," or "coupled to" another element, it can be directly on, attached to, connected to, or coupled to the other element or intervening elements that may be present. On the other hand, when an element is referred to as being "directly on," "directly attached to," "directly connected to," or "directly coupled to" another element, there are no intervening elements present. As used herein, the term "and/or" includes any and all combinations of one or more of the associated listed items.

In this application, the terms first, second, etc. are used to describe various elements, components, regions, layers, and/or sections. However, these elements, components, regions, layers, and/or sections should not be limited by these terms since these terms are only used to distinguish one element, component, region, layer, and/or section from other elements, components, regions, layers, and/or sections that may be present. For example, a first element, component region, layer or section discussed below could be termed a second element, component, region, layer, or section.

In this application, spatial terms, such as "beneath," "below," "lower," "over," "above," "upper," and "beside" (and the like) are used for ease of description to describe one element or feature's relationship to another element(s) or feature(s). The invention, however, is not intended to be limited by the spatial terms. For example, if an example of the invention illustrated in the figures is turned over, elements described as "over" or "above" other elements or features would then be oriented "under" or "below" the other elements or features. Thus, the spatial term "over" may encompass both an orientation of above and below. The device may be otherwise oriented (rotated 90 degrees or at other orientations) and the spatially relative descriptors used herein interpreted accordingly. The terms "conductive" and "non-conductive" relate to the conduction of electricity (a conductor) or the non conduction of electricity (an insulator).

In this application, example embodiments may be described by referring to plan views and/or cross-sectional views which may be ideal schematic views. However, it is understood the views may be modified depending on manufacturing technologies and/or tolerances. Accordingly, the invention is not limited by the examples illustrated in the views, but may include modifications in configurations formed on the basis of manufacturing process. Therefore, regions illustrated in the figures are schematic and exemplary and do not limit the invention.

The subject matter of example embodiments, as disclosed herein, is described with specificity to meet statutory requirements. However, the description itself is not intended to limit the scope of this patent. Rather, the inventors have contemplated that the claimed subject matter might also be embodied in other ways, to include different features or combinations of features similar to the ones described in this document, in conjunction with other technologies. Generally, example embodiments of the invention relate to a fluid detection device usable for detecting fluid excreted by a human body. However, the invention is not limited thereto as the invention may also be usable for detecting fluid(s) excreted by an animal, for example, a horse, a cat, and/or a dog, as well.

FIG. 1 is an exploded view of a pliable fluid detection device 10 according to example embodiments. In its most basic form, the fluid detection device 10 includes a fluid-absorbent non-conductive member 40 sandwiched between a first conductive member 20 and a second conductive member 30. The first and second conductive members 20 and 30 are connected to a voltage source 50 via first and second wires 60 and 70. Because the first and second conductive members 20 and 30 are separated from each other by the non-conductive member 40, the fluid detection device 10 may behave as an open circuit. In other words, the non-conductive member 40 may prevent current from flowing from the first conductive member 20 to the second conductive member 30. It should be noted that the conductive members 20 and 30 do not have to be on opposite sides of the non-conductive member 40. Instead, they can be on the same side of the member 40 so long as they are separated from one another by a portion of the non-conductive member 40.

In example embodiments, the non-conductive member 40 may, for example, be formed of a fluid absorbent material. For example, the non-conductive member 40 may be formed of muslin cloth or gauze. The non-conductive member 40 may also be relatively thin. For example, the non-conductive member 40 must have a thickness such that in its dry state it serves as an electrical insulator and prevents any current from flowing between the electrodes. Preferably the thickness t is about 0.3 mm to about 10 mm, but such thickness is not essential to the invention. This depends on the electrical insulating properties of the non-conducting member, the electric voltage applied to the conducting members or electrodes on either side of the non-conducting member, and the use to which it is put. For example, where small quantities of fluid are expected to trigger an alarm (such as with blood) the insulated distance between opposing conductors would be relatively small. For a less serious example with copious fluid, such as urine, a spacing of 10 mm may be adequate. This voltage must be low enough so as to not create an electric hazard to the patient. This may typically be provided by a battery of three to six volts, but is not limited to these voltages or this source of voltage. The invention, is also not limited to muslin cloth, gauze, or any other material of any particular thickness, as the thickness will depend upon the electrical insulating properties of this material, the electric voltage applied, and the electric current desired. For example, the non-conductive member 40 may be formed of a relatively porous material made from polyolefin, PVC, polyester, urethane, natural or synthetic rubbers or elastomers (for example, porous synthetic rubbers or elastomers that allow body fluid to travel therethrough), and foamed structures. Further yet, the non-conductive member 40 may be a composite structure made from both conductive and non-conductive materials. For example, the non-conductive member 40 may be a fluid absorbing laminated material. Furthermore, the non-conductive member 40 may have a thickness t of less than 1 mm or greater than 3 mm.

A characteristic of the non-conductive member 40 is that it is fluid absorbent and can transport fluid across its thickness t. In other words, the non-conductive member 40 should be configured so that a body fluid, for example, blood or urine, can be absorbed into the material and/or transported across its thickness t.

In example embodiments, the first conductive member 20 may be on a first surface 42 of the non-conductive member 40 and the second conductive member 30 may be on a second surface 44 of the non-conductive member 40. The first surface 42, for example, may be an upper surface of the non-conductive member 40 and the second surface 44, for example, may be lower surface of the non-conductive member 40, or a surface of the non-conductive member 40 that may face a patient's body. In example embodiments, the first and second surfaces 42 and 44 may be separated by the thickness t of the non-conductive member 40. Although the thickness t of the non-conductive member 40 is illustrated as being constant, the invention is not limited thereto. For example, the thickness may be variable.

In example embodiments, the first conductive member 20 may be directly on the first surface 42 of the non-conductive member 40 and the second conductive member 40 may be directly on the second surface 44 of the non-conductive member 40, however, the invention is not limited thereto. For example, there may be intervening layers between either, or both of, the first and second conductive members 20 and 30 and the non-conductive member 40.

Figure 2:
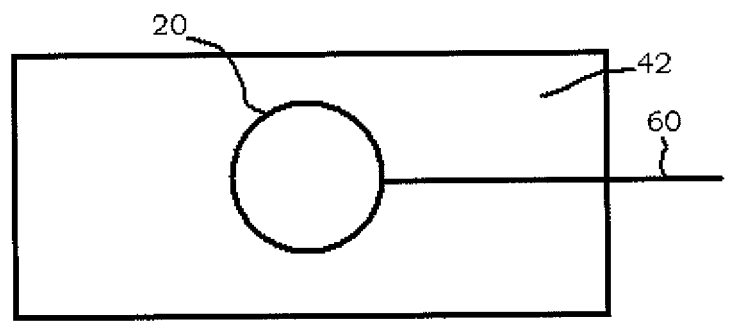
FIGS. 2 and 3 are top and bottom views of the fluid detection device of FIG. 1 in accordance with example embodiments.
Figure 3:
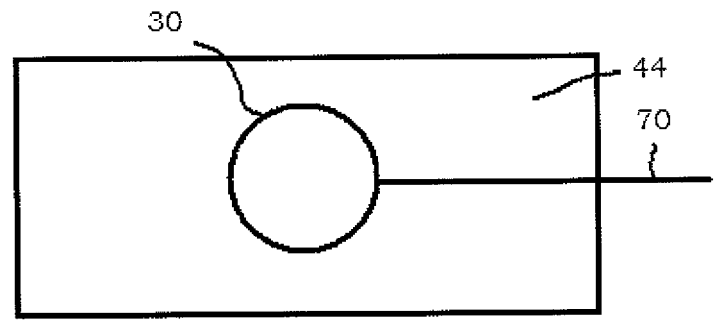

As alluded to previously, the non-conductive member 40 is sandwiched between the first conductive member 20 and the second conductive member 30. In example embodiments, the first and second conductive members 20 and 30 may have substantially the same shape. For example, as illustrated in FIGS. 1-3, the first and second conductive members 20 and 30 may be formed in the shape of a circle. For example, metal wires may be formed in the shape of a circle to form the first and second conductive members 20 and 30. Furthermore, the first and second conductive members 20 and 30 may be arranged so that their profiles either completely or substantially overlap one another when viewed from a direction parallel to the thickness t of the non-conductive member 40, or when looked at from above, below, or any other angle. FIG. 2 illustrates a top view of the fluid detection device 10 having the first conductive member 20 on the first surface 42 of the non-conductive member 40 and FIG. 3 illustrates a bottom view of the fluid detection device 10 having the second conductive member 30 on the second surface 44 of the non-conductive member 40.

Figure 4:
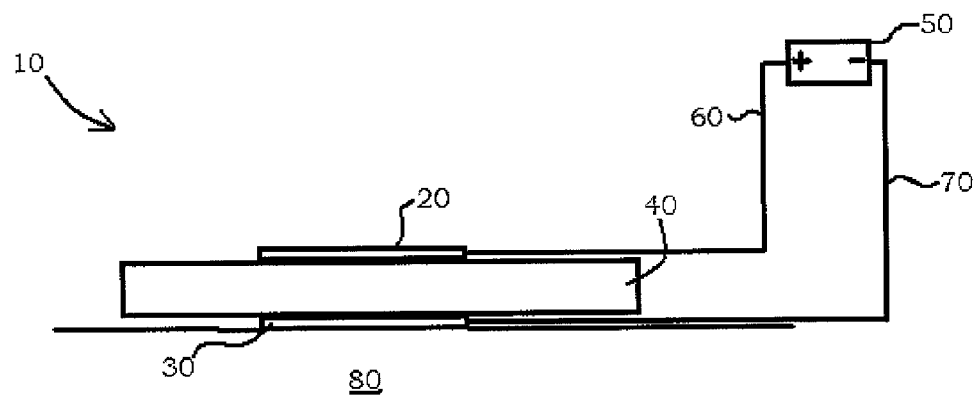
FIG. 4 is a side view of the fluid detection device mounted on skin in accordance with example embodiments.
Figure 5:
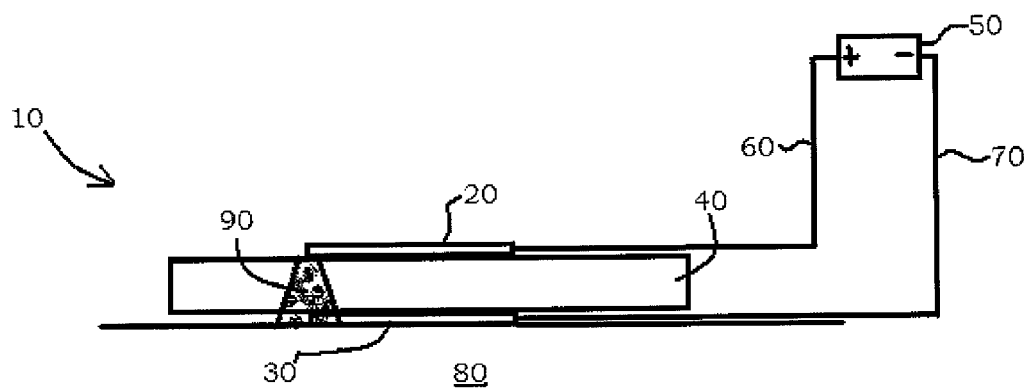
FIG. 5 is a side view of the fluid detection device mounted on skin with body fluid traversing through the fluid detection device in accordance with example embodiments.

FIG. 4 is a side view of the fluid detection device 10 mounted on the skin 80 of a person. FIG. 5 is a side view of the fluid detection device 10 mounted on the skin 80 of a person suffering fluid loss, for example, blood or urine, near a vicinity of the fluid detection device. In FIG. 4, the fluid detection device 10 behaves as an open circuit since non-conductive member 40 prevents current from flowing from the first conductive member 20 to the second conductive member 30. However, when the non-conductive member 40 absorbs and/or transports the body fluid 90 across the thickness t of the non-conductive member 40 as shown in FIG. 5, the body fluid 90 provides a path for current to flow from the first conductive member 20 to the second conductive member 30 because of the electrolytes present in the body fluid 90. Thus, the body fluid 90 absorbed by non-conductive member 40 acts to close the circuit formed by the first and second conductive members 20 and 30 allowing current to flow through the wires 60 and 70. In example embodiments, the current can be sensed, for example, by a current sensing device 55 (see FIG. 1) such as an ammeter. Thus, fluid loss may be detected in accordance with the current sensed by the current sensing device 55.

In example embodiments, the current sensing device 55 may be connected to the circuit including the first conductive member 20, the second conductive member 30, the wires 60 and 70, and the voltage source 50. Thus, body fluids near a vicinity of the fluid detection device 10 may be detected when the current sensing device 55 detects current flowing through the circuit. The current sensing device 55 may be connected to a signal generator 57 configured to generate a signal to alert an interested party, for example, a caregiver or a patient, that the fluid detection device 10 has detected body fluid in the vicinity thereof. The signal generator 57, for example, may be a light generator, a noise generator, a vibration generator, or a combination thereof. For example, the noise generator could be a bell or a buzzer. In addition, the current sensing device 55 could be connected to a computer which could send an electronic message to the interested party to inform the interested party that the body fluid has been detected by the fluid detection device 10. The electronic message could, for example, be an email, a text message, an instant message, or a voice message. The computer or some other device could also keep and store records about the timing of the fluid loss for suitable analysis.

In essence, the conducting members can consist of a bare electrical conductor (without an insulating cover), typically a wire or set of wires, which is kept a small distance apart by the non-conducting member from a second conducting member. The conducting members may consist of uninsulated wires or other shapes made of electrically conducting materials such as copper, brass, or stainless steel, kept apart by a minimal thickness of the non-conducting member. The two conducting members are separated by the non-conducting member in a vertical, horizontal or any other placement. When the body fluid is absorbed by the non-conducting member, the electrical resistance of the non-conducting member will decrease, possibly approaching zero ohms. When this resistance is sufficiently low, measurable and usable electric current will flow between the conducting members. This current can be sensed and measured, and used to trigger and alarm or serve some other useful purpose. This proposal is not restricted to only two electrically conducting members separated by a single non-conducting member. Several conducting members may be layered between non-conducting members, with one conducting member followed by a non conducting member followed by a conducting member followed by a non-conducting member (sandwiched) and so on. Several direct connections between alternating conducting members can serve the purpose of showing when the sandwiched layer is wet enough to allow current flow. In this manner the rate of liquid flow through the sandwiched device could be determined.

Figure 6:
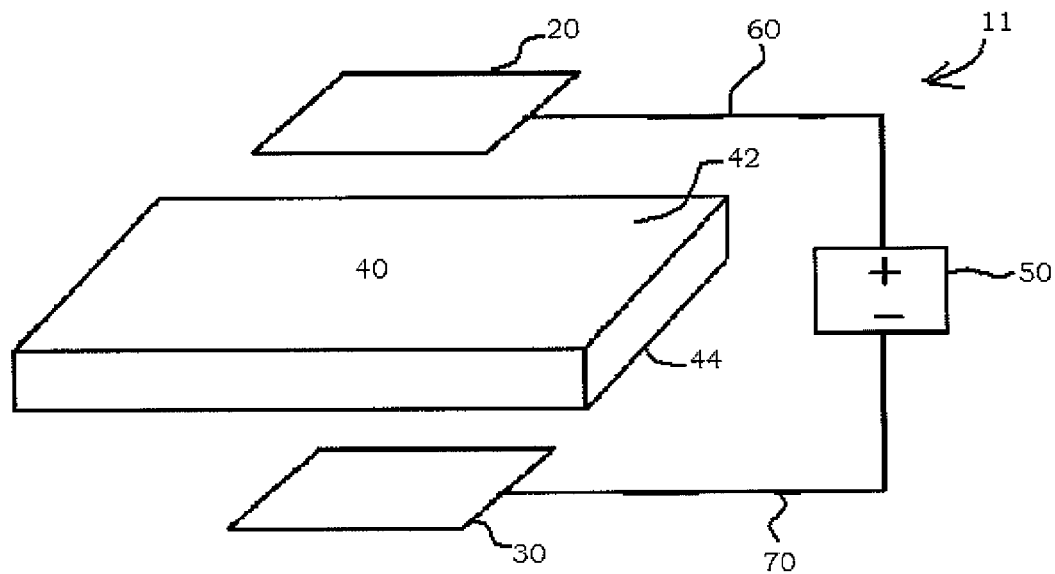
FIG. 6 is an exploded view of a fluid detection device in accordance with example embodiments.
Figure 7:
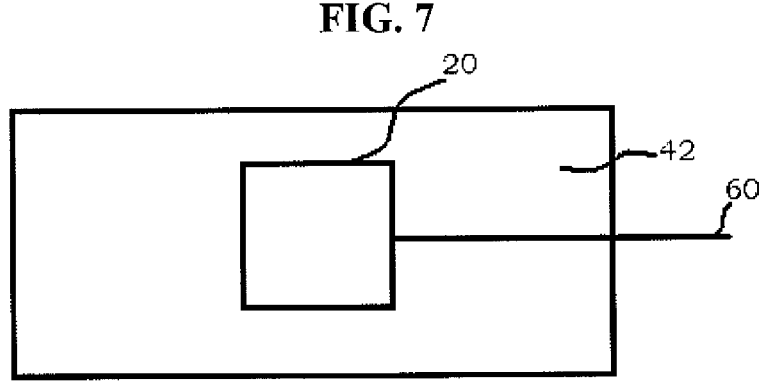
FIGS. 7 and 8 are top and bottom views of the fluid detection device of FIG. 6 in accordance with example embodiments.
Figure 8:
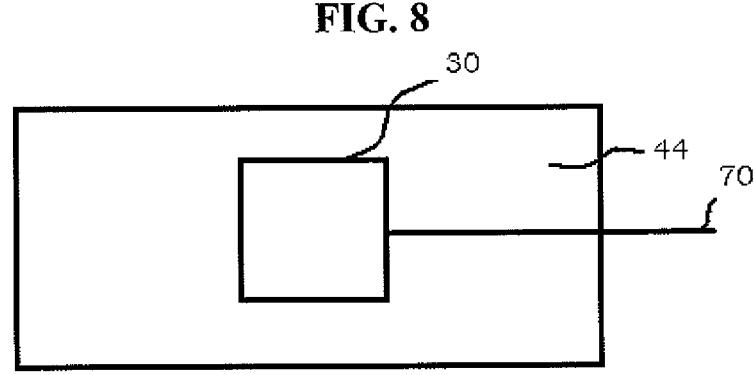

In FIGS. 1-3 the first and second conductive members 20 and 30 are illustrated as including a circular conductive structure, which may be a wire formed in a circular shape, connected to wires 60 and 70. The invention, however, is not limited thereto. In FIGS. 6-8, for example, an example fluid detection device 11 is illustrated. FIG. 6 is an exploded view of the fluid detection device 11 and FIGS. 7 and 8 are top and bottom views of the fluid detection device 11. Unlike the fluid detection device 10 illustrated in FIGS. 1-3, the fluid detection device 11 illustrated in FIGS. 6-8 includes first and second conductive members 20 and 30 which are rectangular in shape. In all other respects, however, the fluid detection device 11 illustrated in FIGS. 6-8 is substantially identical to the fluid detection device 10 illustrated in FIGS. 1-3. Thus a detailed description of the fluid detection device 11 is omitted for the sake of brevity.

Figure 9:
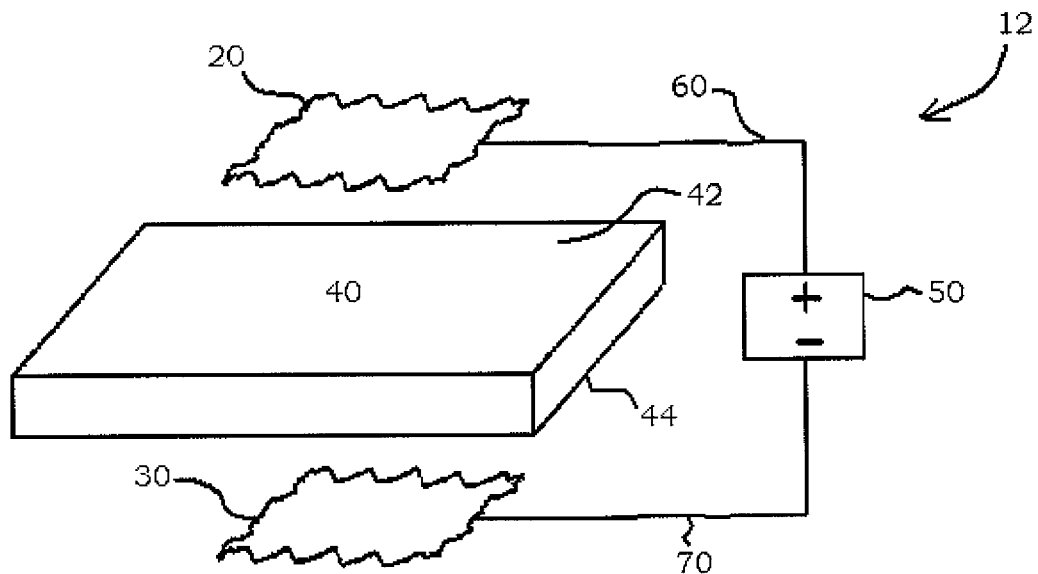
FIG. 9 is an exploded view of a fluid detection device in accordance with example embodiments.
Figure 10:
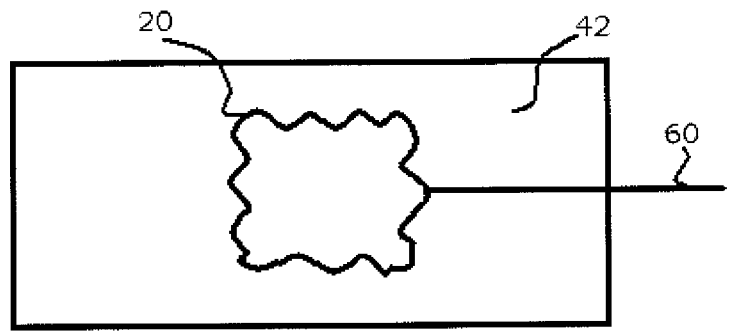
FIGS. 10 and 11 are top and bottom views of the fluid detection device of FIG. 9 in accordance with example embodiments.
Figure 11:
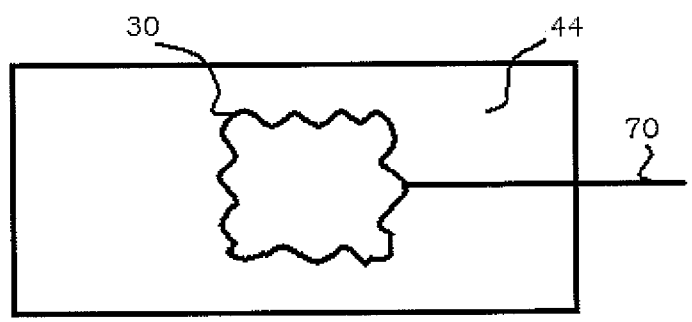

FIGS. 9-11 illustrate another example fluid detection device 12 in accordance with example embodiments. FIG. 9 is an exploded view of the fluid detection device 12 and FIGS. 10 and 11 are top and bottom views of the fluid detection device 12. Unlike the fluid detection device 10 illustrated in FIGS. 1-3, the fluid detection device 12 illustrated in FIGS. 9-11 includes first and second conductive members 20 and 30 which are convoluted in shape. In all other respects, however, the fluid detection device 12 illustrated in FIGS. 9-11 is substantially identical to the fluid detection device 10 illustrated in FIGS. 1-3. Thus a detailed description of the fluid detection device 12 is omitted for the sake of brevity.

Figure 12:
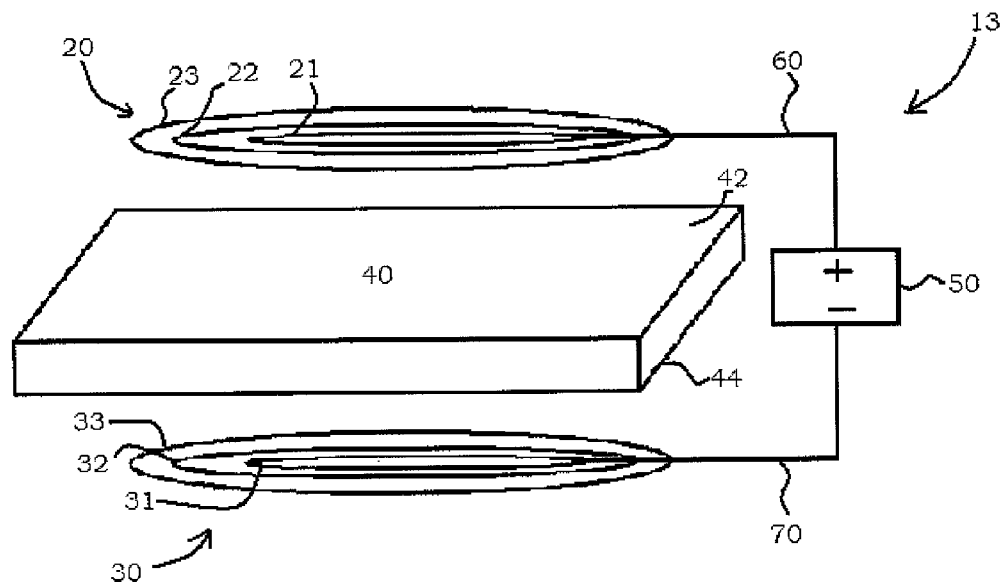
FIG. 12 is an exploded view of a fluid detection device in accordance with example embodiments.
Figure 13:
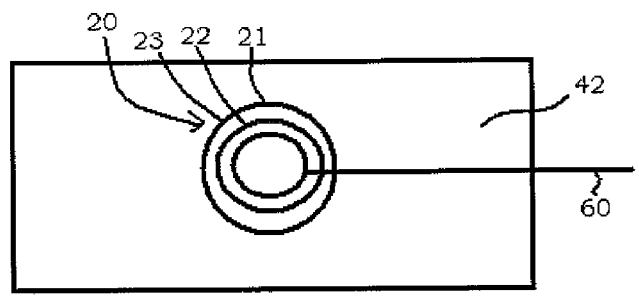
FIGS. 13 and 14 are top and bottom views of the fluid detection device of FIG. 12 in accordance with example embodiments.
Figure 14:
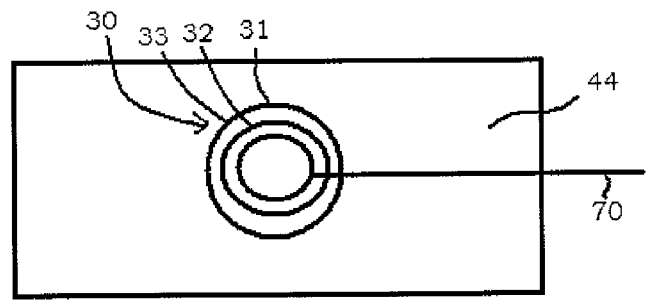

FIGS. 12-14 illustrate another example fluid detection device 12 in accordance with example embodiments. FIG. 12 is an exploded view of the fluid detection device 13 and FIGS. 13 and 14 are top and bottom views of the fluid detection device 13. Unlike the fluid detection device 10 illustrated in FIGS. 1-3, the fluid detection device 13 illustrated in FIGS. 12-14 includes first and second conductive members 20 and 30 which are comprised of a plurality of concentric rings. For example, FIGS. 12-13 illustrate the first conductive member 20 has having three rings 21, 22, and 23. Similarly, as illustrated in FIGS. 12 and 14, the second conductive member 30 has three rings, 31, 32, and 33. In example embodiments, the rings 21, 22, and 23 of the first conductive member 20 may be electrically connected together. For example, the rings 21, 22, and 23 may be electrically connected to one another via the wire 60. Similarly, the rings 31, 32, and 33 of the second conductive member 30 may also be electrically connected to one another. For example, the rings 31, 32, and 33 may be electrically connected to one another via the wire 70.

In example embodiments, the rings 21, 22, 23, 31, 32, and 33 may be formed from wires which may be formed, for example, bent, into a circular shape. Example embodiments, however, are not limited thereto. For example, the rings could be formed on the non-conductive member 40 via a printing process which sprays a conductive material onto the non-conductive member 40 to form the plurality of rings. As yet another example, the rings may simply be painted onto the non-conductive member 40 via a painting process.

In FIG. 12, the plurality of rings of the first electrically conductive member 20 may be spaced relatively close to one another. For example, the diameter of the second ring 22 may be about 2 mm larger than the diameter of the first ring 21. Similarly, the diameter of the third ring 23 may be about 2 mm larger than the diameter of the second ring 22. In example embodiments, the plurality of rings of the second electrically conductive member 30 may be likewise spaced relatively close to one another. For example, the diameter of the second ring 32 may be about 2 mm larger than the diameter of the first ring 31 and the diameter of the third ring 33 may be about 2 mm larger than the diameter of the second ring 32. Although the differences in the diameters of rings 21 and 22, 22 and 23, 31 and 32, and 32 and 33 has been described as being about 2 mm, the invention is not limited thereto. For example, the differences between the diameters of rings 21 and 22, 22 and 23, 31 and 32, and 32 and 33 may be more or less than about 2 mm.

In example embodiments, the sizes of the plurality of rings associated with the first conductive member 20 may be substantially the same as the sizes of the plurality of rings associated with the second conductive member 30. For example, a diameter of the first ring 21 of the first electrically conductive member 20 may be substantially the same as a diameter of the first ring 31 of the second conductive member 30. Similarly, a diameter of the second ring 22 of the first electrically conductive member 20 may be substantially the same as a diameter of the second ring 32 of the second conductive member 30. Similar yet, a diameter of the third ring 23 of the first electrically conductive member 20 may be substantially the same as a diameter of the third ring 33 of the second conductive member 30.

In example embodiments, as shown in FIGS. 12-14, the plurality of rings of the first conductive member 20 and the plurality of rings of the second conductive member 30 may be arranged on the first side 42 of the non-conductive member 40 and the second side 44 of the non-conductive member 40, respectively. Further yet, the plurality of rings of the first conductive member 20 and the plurality of rings of the second conductive member 30 may be arranged to substantially overlap one another. For example, the first ring 21 of the first conductive member 20 may substantially overlap the first ring 31 of the second conductive member 30 when viewed from a direction parallel to the thickness of the non-conductive member 40. Similarly, the second ring 22 of the first conductive member 20 may substantially overlap the second ring 32 of the second conductive member 30. Similar yet, the third ring 23 of the first conductive member 20 may substantially overlap the third ring 33 of the second conductive member 30.

In the fluid sensing device 13 of FIGS. 12-14, because the first and second conductive members 20 and 30 include a plurality of rings, the area in which fluid loss may be detected may be increased when compared to the fluid sensing device 10 of FIGS. 1-3. It should be noted that although the fluid detecting device 13 of FIGS. 12-14 is illustrated as having a first conductive member 20 with three electrically conductive rings 21, 22, and 23, the invention is not limited thereto. For example, the first conductive member 20 may have two rings or more than three rings. Similarly, the second conductive member 30 may have two rings or more than three rings.

Figure 15:
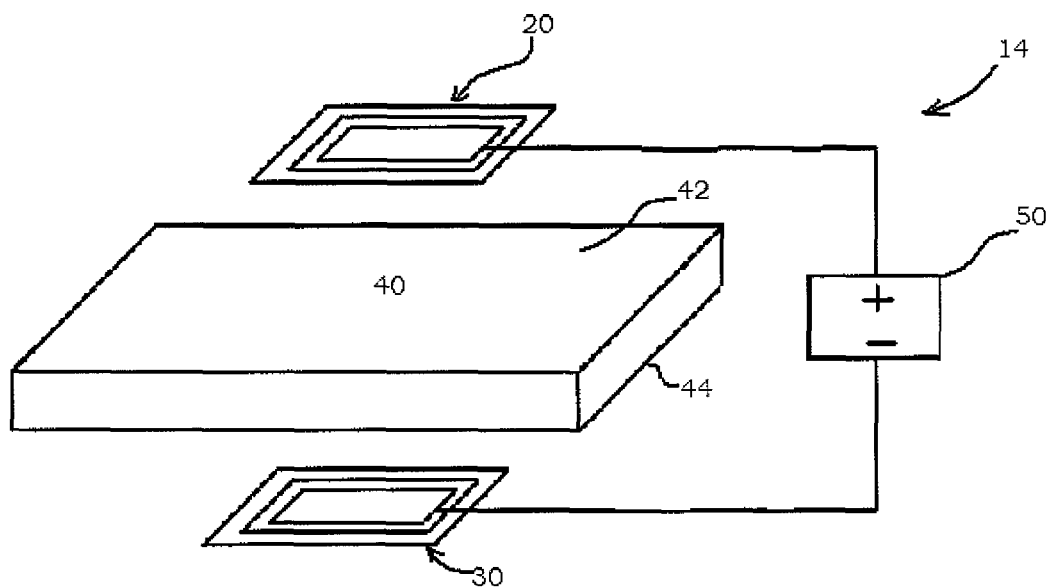
FIG. 15 is an exploded view of a fluid detection device in accordance with example embodiments.
Figure 16:
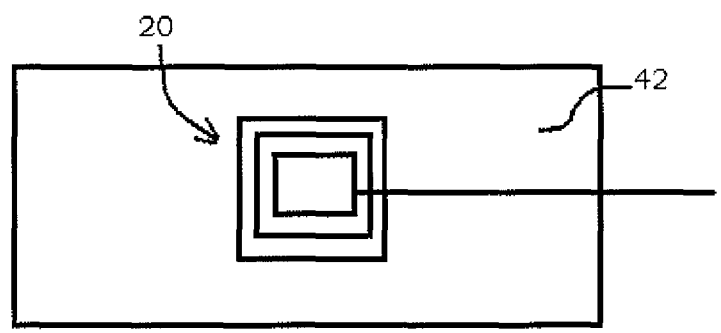
FIGS. 16 and 17 are top and bottom views of the fluid detection device of FIG. 15 in accordance with example embodiments.
Figure 17:
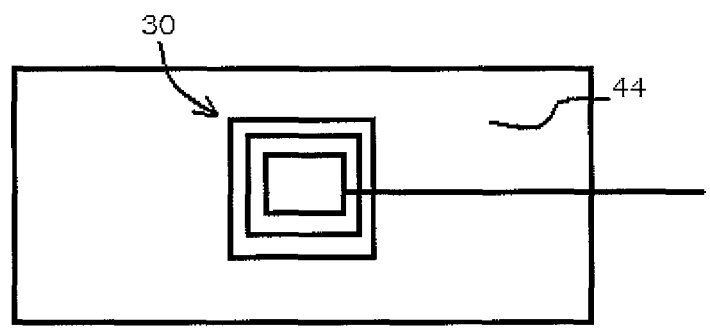

FIGS. 15-17 illustrate another example fluid detection device 14 in accordance with example embodiments. In FIGS. 15-17, FIG. 15 is an exploded view of the fluid detection device 14 and FIGS. 16 and 17 are top and bottom views of the fluid detection device 14. Unlike the fluid detection device 13 illustrated in FIGS. 12-14, the fluid detection device 14 illustrated in FIGS. 15-17 includes first and second conductive members 20 and 30 having a plurality of rectangular (for example, square) loops. In all other respects, however, the fluid detection device 14 illustrated in FIGS. 15-17 is substantially identical to the fluid detection device 13 illustrated in FIGS. 12-14. Thus a detailed description of the fluid detection device 14 is omitted for the sake of brevity.

Figure 18:
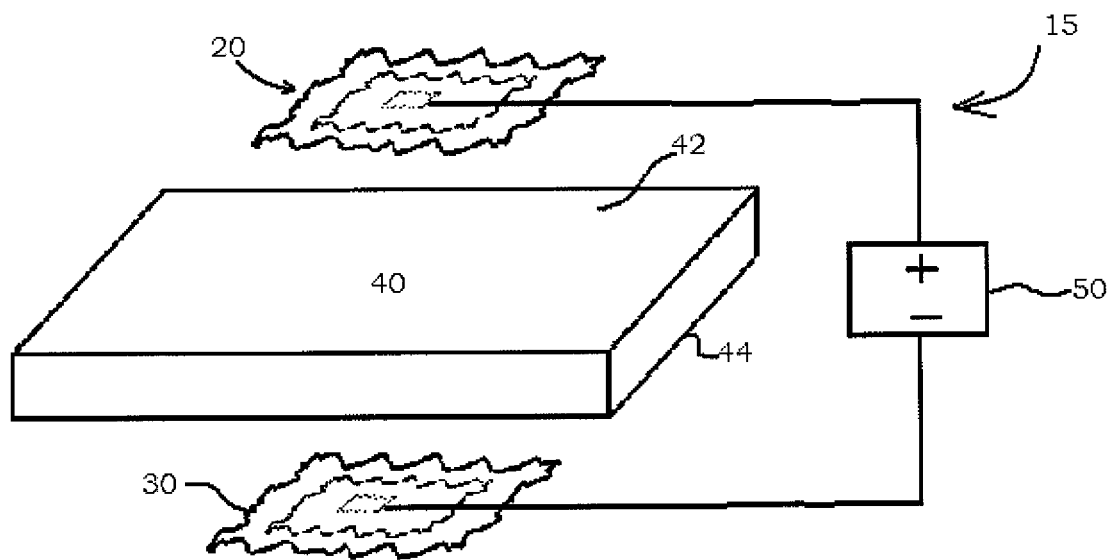
FIG. 18 is an exploded view of a fluid detection device in accordance with example embodiments.
Figure 19:
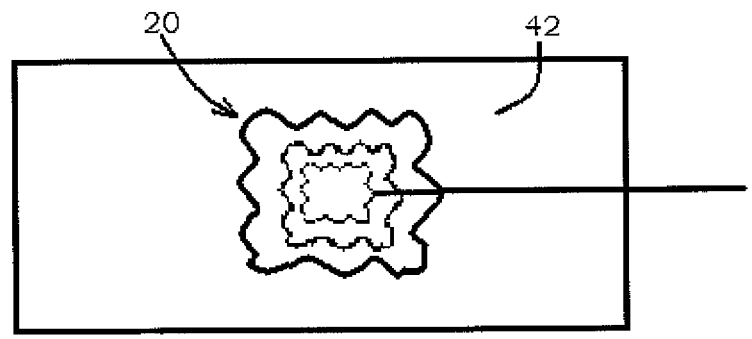
FIGS. 19 and 20 are top and bottom views of the fluid detection device of FIG. 18 in accordance with example embodiments.
Figure 20:
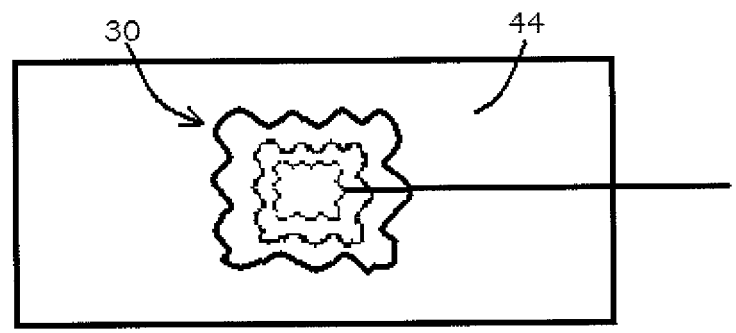

FIGS. 18-20 illustrate another example fluid detection device 15 in accordance with example embodiments. In FIGS. 18-20, FIG. 18 is an exploded view of the fluid detection device 15 and FIGS. 19 and 20 are top and bottom views of the fluid detection device 15. Unlike the fluid detection device 13 illustrated in FIGS. 12-14, the fluid detection device 15 illustrated in FIGS. 18-20 includes first and second conductive members 20 and 30 having a plurality of convoluted loops. In all other respects, however, the fluid detection device 15 illustrated in FIGS. 18-20 is substantially identical to the fluid detection device 13 illustrated in FIGS. 12-14. Thus a detailed description of the fluid detection device 15 is omitted for the sake of brevity.

Figure 21:
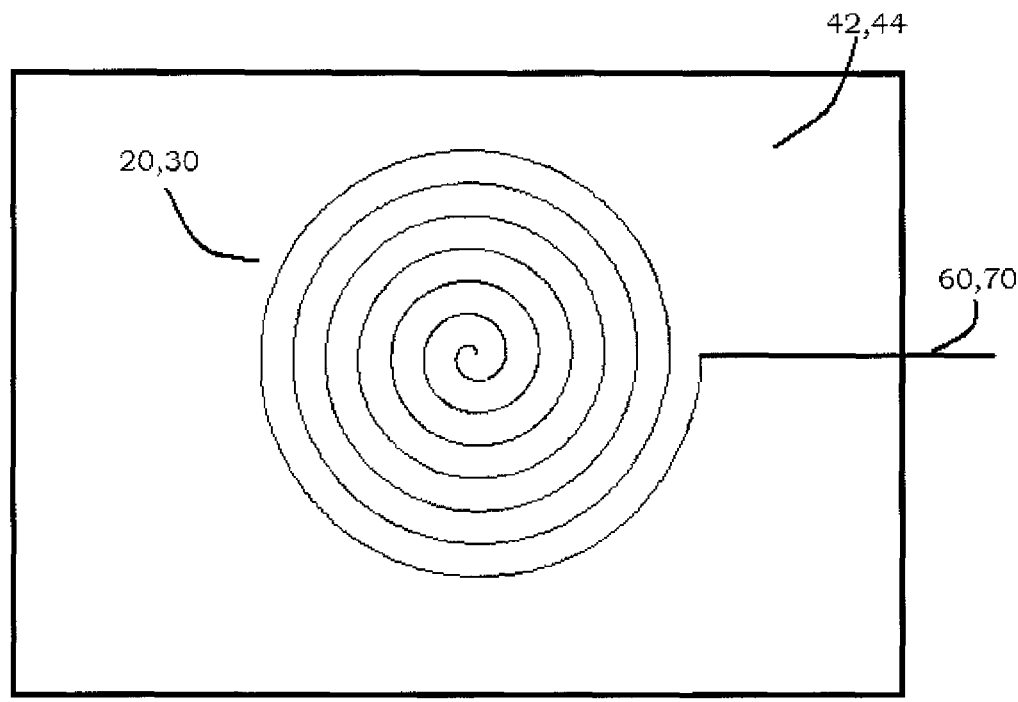
FIG. 21 is a view of a first conductive member and second conductive member on a non-conductive member in accordance with example embodiments.
Figure 22:
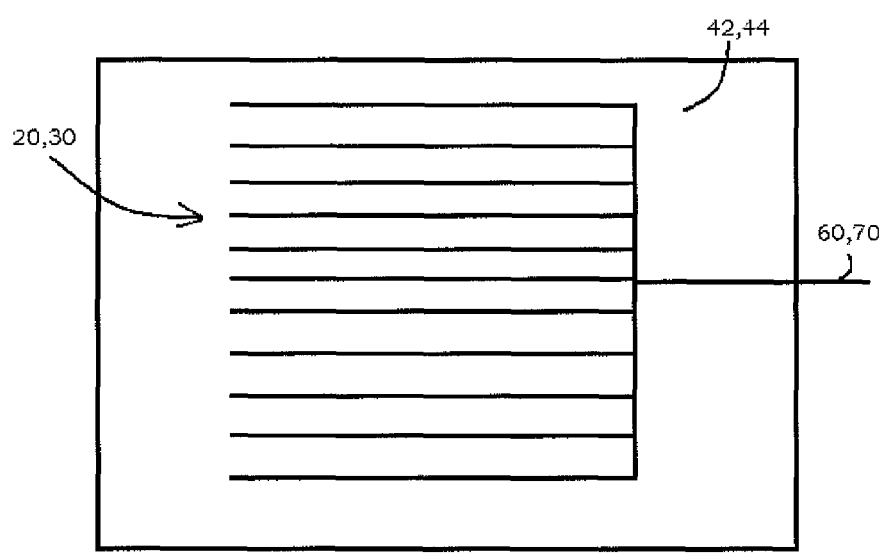
FIG. 22 is a view of a first conductive member and second conductive member on a non-conductive member in accordance with example embodiments.

Although example embodiments have illustrated a fluid detection device as having a first conductive member and a second conductive member as having one or more loops, example embodiments are not limited thereto. For example, the first and second conductive members 20 and 30 could have a spiral configuration as illustrated in FIG. 21. As another example, the first and second conductive members 20 and 30 could be comprised of a series of parallel lines arranged on the first and second surfaces of the non-conductive member 40. In this latter case, the parallel lines may be electrically connected together as shown in FIG. 22.

Figure 23:
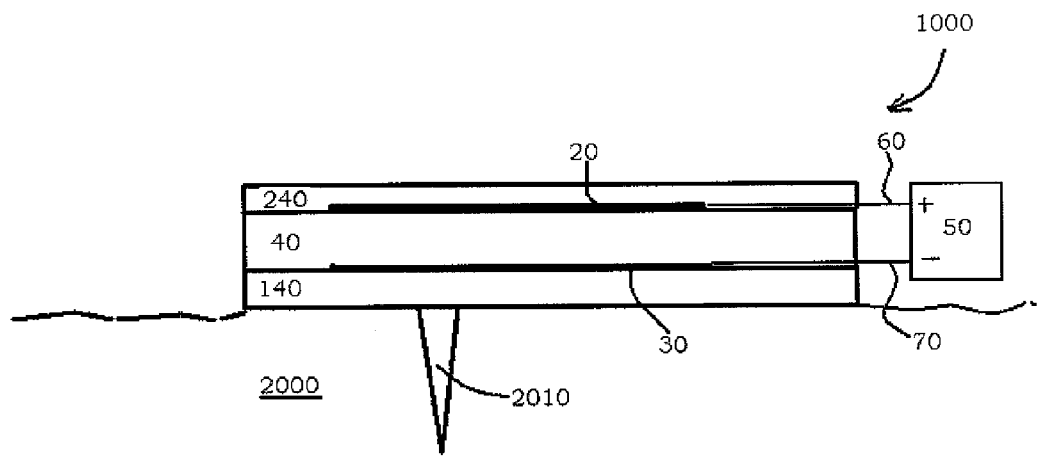
FIG. 23 is a view of a patch in accordance with example embodiments.

FIG. 23 is an example of a fluid detection device implemented as a patch 1000. The patch 1000, for example, may be mounted on the skin 2000 of a patient near a site 2010 which may present a fluid loss concern for a given patient. For example, the site 2010 may be an incision which was recently closed after an operation has been performed. Alternatively, the site 2010 may be associated with an access point provided in patients undergoing either chemotherapy or dialysis. Although FIG. 23 illustrates the patch 1000 as being on the skin 2000 of a patient, the invention is not limited thereto. For example, rather than attaching the patch 1000 to the skin of a patient, the patch 1000 may be attached to an article of clothing to detect whether the article of clothing is (or has been) exposed to body fluid, for example, blood or urine.

In example embodiments, the patch 1000 includes the previously described non-conductive member 40 sandwiched between the previously described first and second conductive members 20 and 30. Thus, the patch 1000 includes a non-conductive member 40 which is capable of transporting a body fluid across its thickness. Furthermore, the patch 1000 includes first and second conductive members 20 and 30 that may resemble a single circular loop, a plurality of concentric loops, a single rectangular loop, a plurality of concentric rectangular loops, a single convoluted loop, a plurality of concentric convoluted loops, a spiral, or a series of parallel lines, as has been previously described. Example embodiments, however, are not limited thereto, as the first and second conductive members 20 and 30 may have other forms not specifically described, but in accordance with, the previous examples. For example, the first and second conductive members 20 and 30 could be comprised of a plurality of wires arranged in a grid pattern. In example embodiments, the first and second conductive members 20 and 30 may be connected to a voltage source 50 via wires 60 and 70. The voltage source 50, for example, may be a battery.

In addition to the aforementioned features, the patch 1000 may also include a first additional layer 140 between the non-conductive layer 40 and the skin 2000. The first additional layer 140 may allow fluid to travel across its thickness. The first additional layer 140, for example, may be a cotton material, for example, muslin cloth or gauze. The first additional layer 140, however, is not limited to muslin cloth or gauze. For example, the first additional layer 140 may be formed of a relatively porous material made from polyolefin, PVC, polyester, urethane, natural or synthetic rubbers or elastomers, and foamed structures. Further yet, the first additional layer 140 may be a composite structure made from both conductive and non-conductive materials. For example, the first additional layer 140 may be a fluid absorbing laminated material. The first additional layer 140 may also include an adhesive thereon. The adhesive may act to bond the patch 1000 to the skin 2000 of the patient, or to another object, for example, medical dressing or clothing.

The patch 1000 may also include a second additional layer 240 on the non-conductive member 40. The second additional layer 240 may or may not be a fluid absorbable material. For example, the second additional layer 240 may be plastic in order to protect the circuitry of the patch from fluid that may not be of interest to a person wearing the patch 1000. However, example embodiments are not limited thereto as the second additional layer 240 may alternatively be fluid absorbent.

Figure 24:
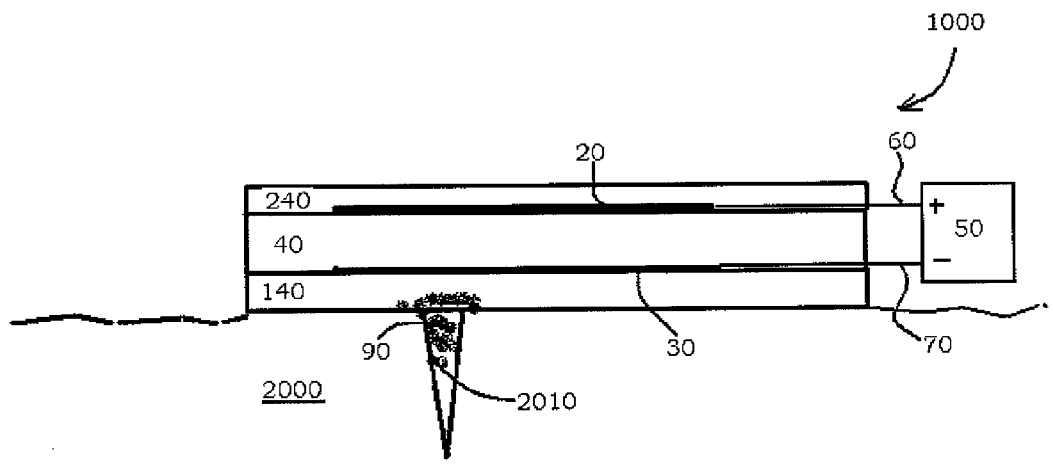
FIGS. 24-27 are views of the patch having body fluid traversing therethrough in accordance with example embodiments.

FIGS. 24-27 illustrate a body fluid 90 flowing from the skin 2000 and through the patch 1000. In FIG. 24, for example, the body fluid 90, which may, for example, be blood, may collect at the site 2010 and may exit the body through the site 2010. In FIG. 24, although the first and second conductive members 20 and 30 are connected to a voltage source 50, electrical current does not flow due to the non-conductive member 40 being arranged therebetween.

Figure 25:
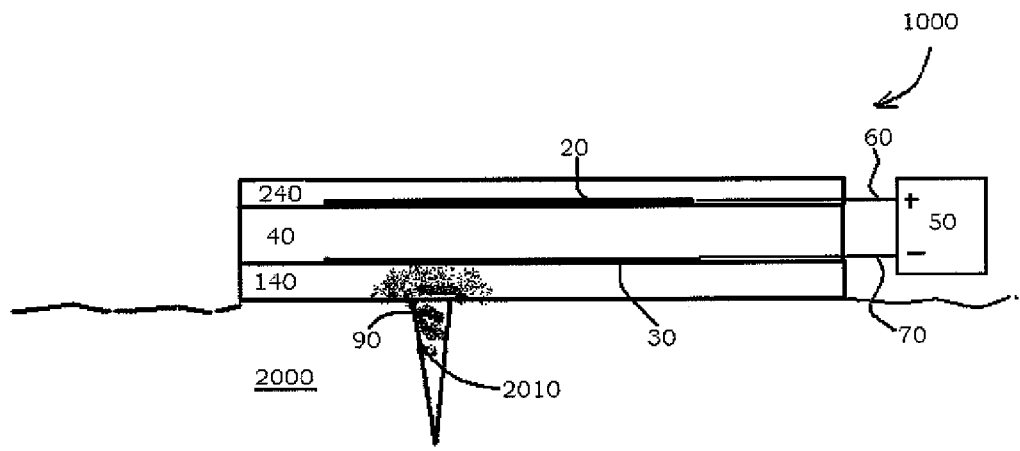
Figure 26:
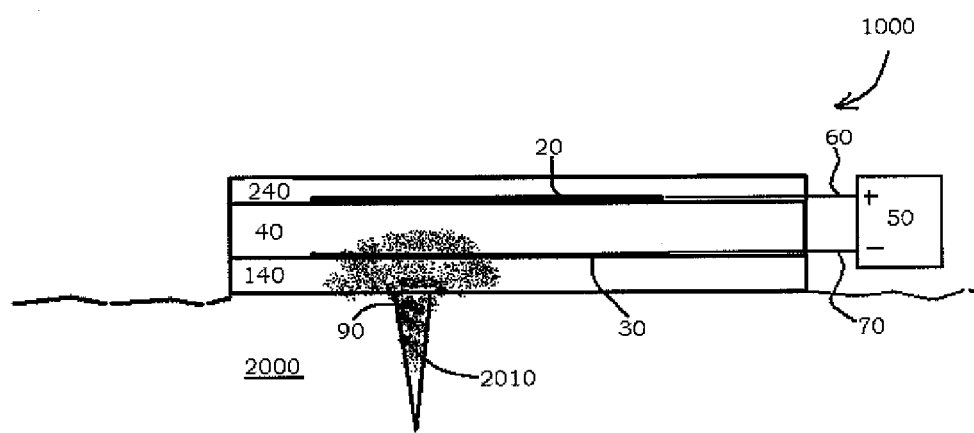
Figure 27:
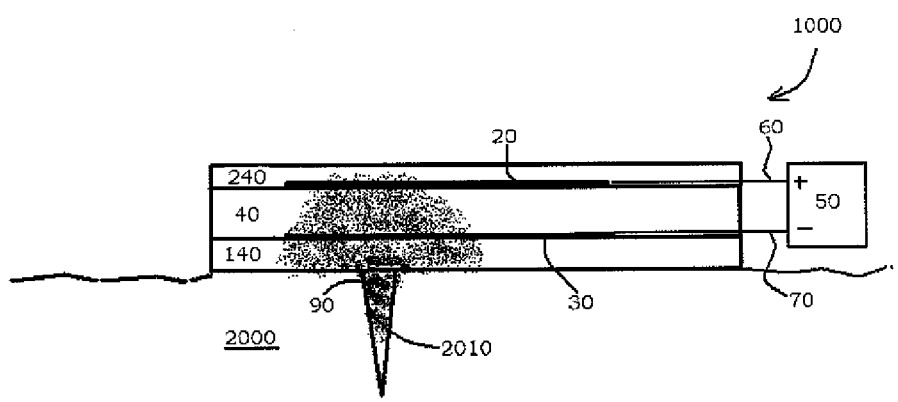

If the body fluid 90 continues to collect at the site 2010, the body fluid 90 may move through the first additional layer 140 and into the non-conductive member 40, as shown in FIGS. 24-26. In FIGS. 24-26, however, body fluid has not traversed completely through the thickness of the non-conductive member 40, thus, current from the first conductive member 20 to the second conductive member 30 still does not flow. However, if the body fluid 90 traverses through the thickness of the non-conductive member 40 and to the first conductive member 20, as shown in FIG. 27, the electrolytes in the body fluid 90 act as a pathway for electrons to flow from the first conductive member 20 to the second conductive member 30. Thus, as shown in FIG. 27, current may flow through the circuit formed by the first conductive member 20, the second conductive member 30, the wires 60 and 70, and the voltage source 50.

As previously described, a current sensing device may be connected to the circuit including the first conductive member 20, the second conductive member 30, the wires 60 and 70, and the voltage source 50. Thus, body fluids in the patch 1000 may be detected when the current sensing device senses current flowing through the circuit. The current sensing device may be connected to a signal generator configured to generate a signal to alert an interested party, for example, a caregiver or a patient, that the patch has detected body fluid in the vicinity thereof. The signal generator, for example, may be a light, a noise generator, or vibration generator, or a combination thereof. For example, the noise generator could be a bell or a buzzer. In addition, the current sensing device could be connected to a computer which could send an electronic message to the interested party to inform the interested party that the body fluid has been detected in the patch. The electronic message could, for example, be an email, a text message, an instant message, or a voice message. The measurements could also be recorded and stored by the computer for further analysis.

Figure 28:
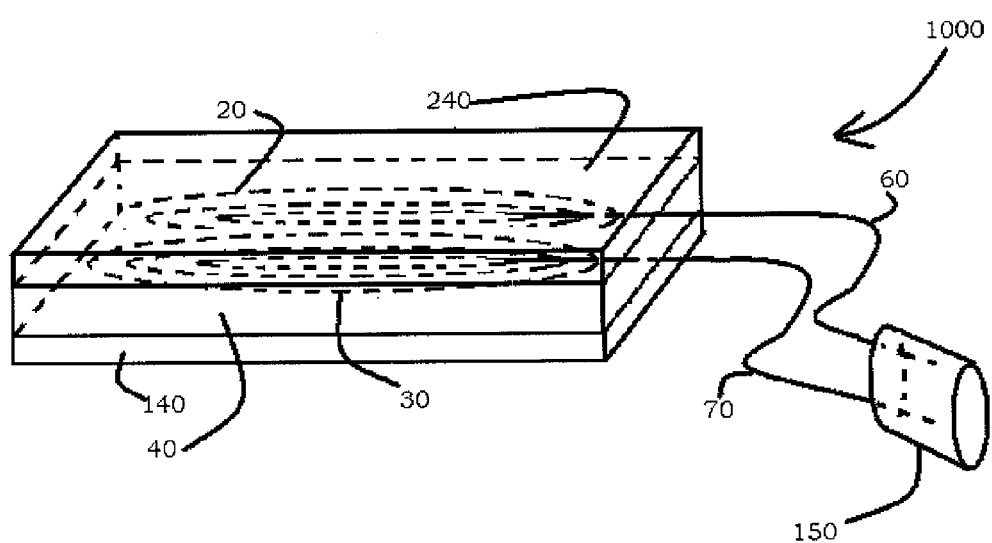
FIG. 28 is a view of a patch in accordance with example embodiments

In example embodiments, the voltage source 50 may be incorporated into the patch 1000, for example, as a battery. However example embodiments are not limited thereto. For example, rather than directly connecting wires 60 and 70 to a voltage source 50, the first and second wires could terminate in a female socket 150 as shown in FIG. 28. The female socket 150 could connect to a male socket which in turn is connected to a voltage source, for example, a battery. Terminating the wires 60 and 70 in a female socket 150 may offer the flexibility of extending the circuit.

In example embodiments, the first and second conductive members 20 and 30 and the wires 60 and 70 may be exposed to body fluids which could rust these members in a relatively short period of time. Thus, in order to prevent these members from acquiring rust, the first and second conductive members 20 and 30 and the wires 60 and 70 may be made from rust resistant materials, for example, 316 or 317 stainless steel. However, example embodiments are not limited thereto as one skilled in the art would recognize several suitable materials usable for the first and second conductive members 20 and 30 and/or the wires 60 and 70.

Figure 29:
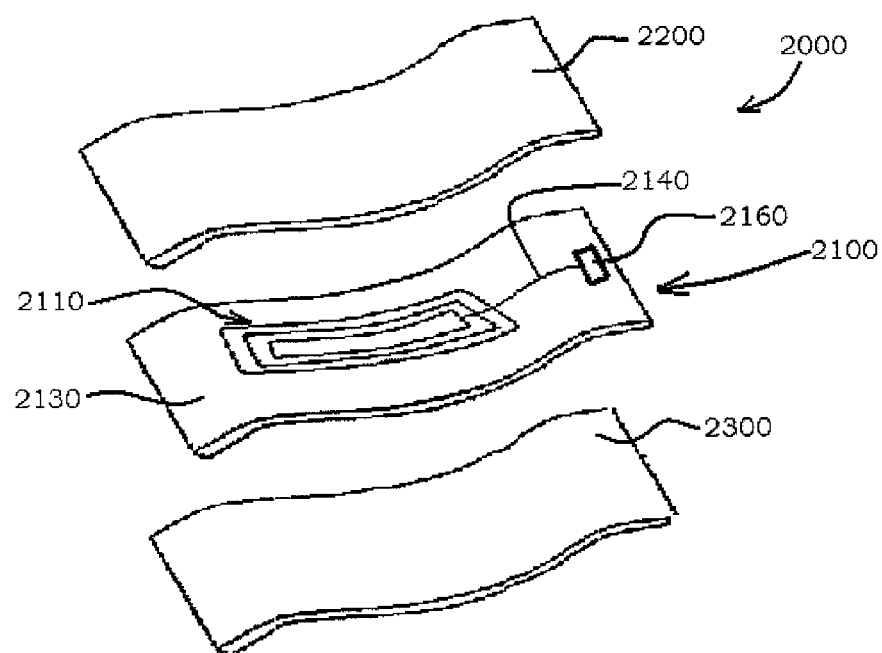
FIG. 29 is a view of a wrap in accordance with example embodiments.
Figure 30:
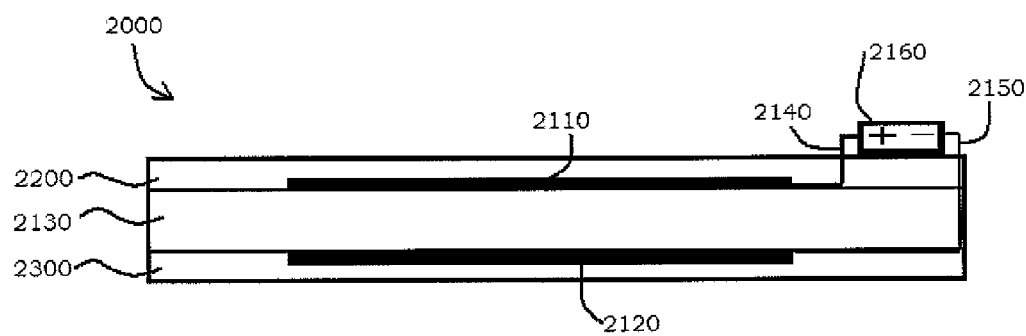
FIG. 30 is a side view of the wrap in accordance with example embodiments.

In example embodiments, the fluid detection devices may be implemented in more than a patch form. For example, the fluid detection devices could be implemented in the form of a wrap that may be applied to a person or animal. FIG. 29, for example, is an exploded view of a wrap 2000 that is provided with a fluid detection device 2100. FIG. 30 is a cross-section view of the wrap 2000. As shown in FIGS. 29 and 30, the wrap 2000 may include an upper layer 2200 and a lower layer 2300 which may sandwich the fluid detection device 2100 therebetween. In example embodiments, at least one of the upper layer 2200 and the lower layer 2300 may be placed next to a person's or animal's skin and the layer placed next to the person's or animal's skin may be made of a fluid absorbable material, for example, muslin.

In example embodiments, the fluid detection device 2100 may include a non-conductive member 2130 sandwiched between a first conductive member 2110 and a second conductive member 2120. The first conductive member 2110 may be comprised of a plurality of concentric loops that are electrically connected to each other via a wire 2140. The wire 2140 may, in turn, may connect the first conductive member 2110 to a voltage source 2160, for example, a battery. The second conductive member 2120 may be comprised of a plurality of concentric loops that are electrically connected to one another via a wire 2150. The wire 2150 may, in turn, connect the second conductive member 2120 to the voltage source 2160. As in the previous embodiments, the plurality of concentric loops of the first conductive member 2110 may substantially overlap the plurality of concentric loops of the second conductive member 2120. As in the previous examples, the non-conductive layer 2010 may be made of a fluid absorbable material that may allow body fluid to traverse the thickness thereof.

As in the previous examples, current may not flow around the circuit formed by the voltage source 2160, the first and second conductive members 2110 and 2120, and the wires 2140 and 2150 due to the non-conductive member 2130 being arranged between the first and second conductive members 2110 and 2120. However, in the event body fluid is absorbed through the thickness of the non-conductive member 2130, current may flow through the circuit due to the electrolytes present in the body fluid. As in the previous embodiments, the current may be sensed by a current sensing device and the sensed current may cause a signal to be sent to signal generator to alert an interested party to the condition of the person wearing the wrap 2000.

Figure 31:
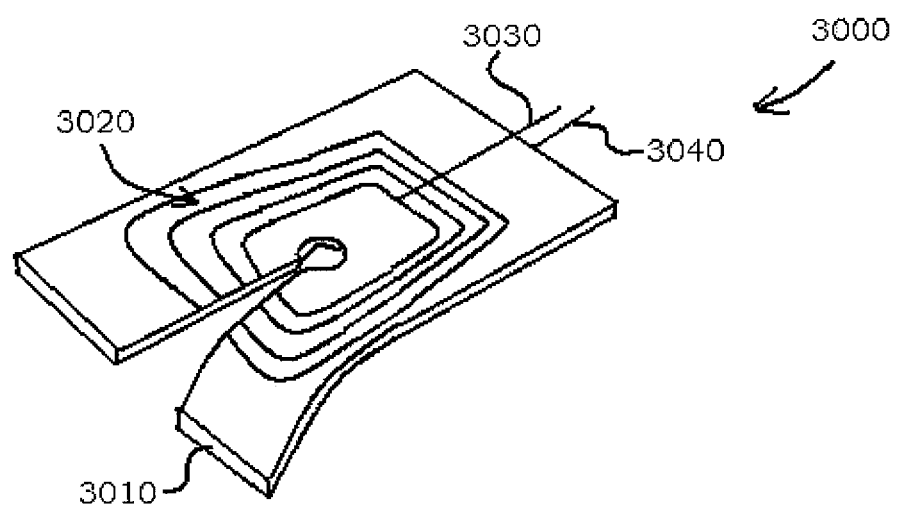
FIG. 31 is a view of a fluid detection device in accordance with example embodiments.

FIG. 31 is another example of a fluid detection device 3000 in accordance with example embodiments. In FIG. 31, the fluid detection device 3000 is illustrated as having a non-conductive member 3010 sandwiched between a first conductive member 3020 and a second conductive member (not shown). The first conductive member 3020 and the second conductive member may be comprised of a plurality of concentric electrically conductive loops which substantially overlap one another as described in the previous example embodiments. As in the previous embodiments, the plurality of electrically conductive loops of the first conductive member 3020 may be electrically connected to one another via a wire 3030. Similarly, the plurality of conductive loops of the second conductive member may be connected to one another via a wire 3040. The wires 3030 and 3040 may in turn be connected to a voltage source.

The fluid detection device 3000 may be substantially similar to the previously disclosed embodiments, thus, a detailed description thereof is omitted for the sake of brevity. However, unlike the previous embodiments, the fluid detection device 3000 includes a gap (or slit) that transects the first conductive member 3020, the non-conductive member 3010, and the second conductive member. Such a gap (or slit) may allow the fluid detection device to easily fit around a structure, for example, a tube extending from a persons body. Such a gap (or slit) may be incorporated in any one of the previous embodiments in the manner presented in FIG. 31.

Figure 32:
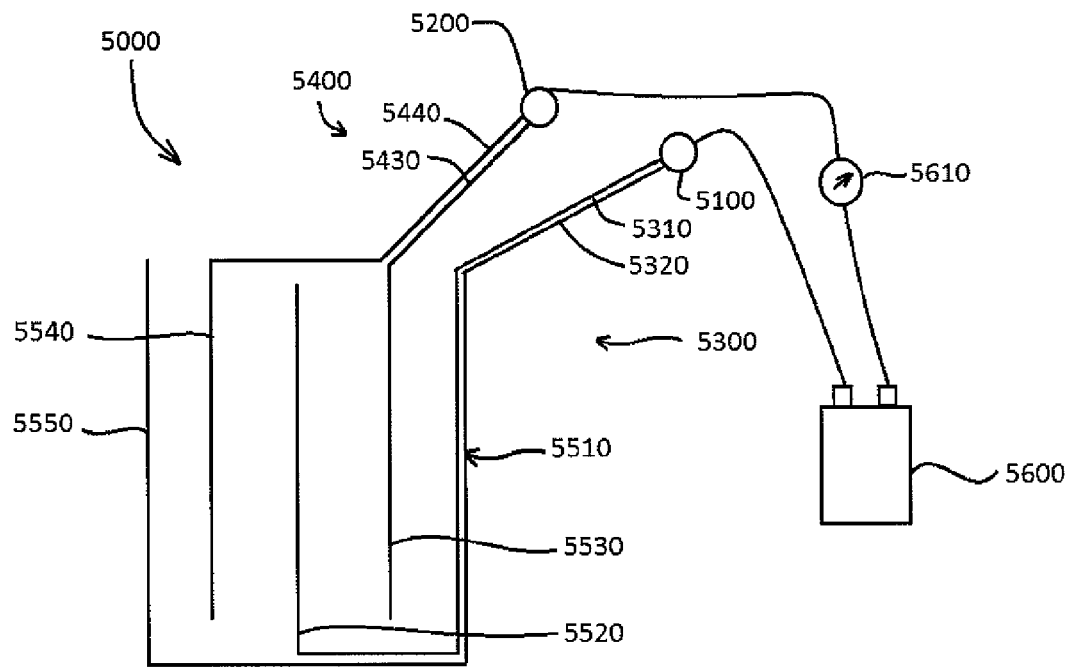
FIG. 32 is a view of a fluid detection device in accordance with example embodiments.

FIG. 32 is an example of a sensor system 5000 in accordance with example embodiments. As shown in FIG. 32, the sensor system 5000 may include a first connector 5100, a second connector 5200, a voltage source 5600, and a detector 5610 which may be configured to detect current flowing through the sensor system 5000. In example embodiments, the first connector 5100 and the second connector 5200 may be, but are not limited to, snaps, clips, or buttons. In example embodiments, the voltage source 5600 may be, but is not limited to, a battery or a low voltage power supply attached to a wall socket connected to an AC source. In example embodiments the detector 5610 may be, but is not limited to, a current detector such as an ammeter.

In example embodiments, the sensor system 5000 may include at least one conductive member 5300 connected to first connector 5100 and at least one conductive member 5400 connected to the second connector 5200. The at least one conductive member 5300 attached to the first connector 5100, for example, may include first wire 5310 and a second wire 5320 and the at least one conductive member 5400 attached to the second connector 5200 may include a third wire 5430 and a fourth wire 5440. In example embodiments, the first, second, third, and fourth wires 5310, 5320, 5430, and 5440 may be made of a metal, for example, copper or aluminum. In example embodiments, the number of wires connected to the first and second connector 5100 and 5200 are not intended to be a limiting feature of example embodiments since there may be more than two wires or less than two wires connected to the first connector 5100 or the second connector 5200.

As shown in FIG. 32, the sensor system 5000 may include a sensing area comprised of a first leg 5510, a second leg 5520, a third leg 5530, a fourth leg 5540 and a fifth leg 5550. The first leg 5510 may be comprised of the first and second wires 5310 and 5320. The first and second wires 5310 and 5320 may or may not be directly connected to each other. Furthermore, portions of the first and second wires 5310 and 5320 may be slightly spaced apart from one, for example, by about 1 mm. In example embodiments, as shown in FIG. 32, portions of the first wire 5310 and the second wire 5320 may be substantially parallel with one another and the substantially parallel portions may form the first leg 5510. In example embodiments, the first wire 5310 may extend to form the second leg 5520 and the second wire 5320 may extend to form the fifth leg 5550. In example embodiments, the third wire 5430 may extend to form the third leg 5530 and the fourth wire 5440 may extend to form the fourth leg 5540. Thus, the sensing area may be comprised of a first plurality of legs (5510, 5520, and 5550) and a second plurality of legs (5530 and 5540) which are alternatively arranged. Furthermore, the first plurality of legs (5510, 5520, and 5550) may be formed by a first plurality of wires (5310, 5320) and the second plurality of legs (5530, 5540) may be formed by a second plurality of wires (5430 and 5440). Further yet, the first plurality of wires (5310, 5320) may be connected to the first connector 5100 and the second plurality of wires (5430, 5440) may be connected to the second connector 5200.

In example embodiments, each of the first, second, third, fourth, and fifth legs 5510, 5520, 5530, 5540, and 5550 may be substantially parallel to each other and may be spaced about 1 cm apart from one another. Example embodiments, however, are not limited thereto as first, second, third, fourth, and fifth legs 5510, 5520, 5530, 5540, and 5550 are not required to be parallel with one another and may be separated by distances greater or less than about 1 cm.

In example embodiments, the at least one conductive member 5300 connected to the first connector 5100 has been described as being comprised of a first wire 5310 and a second wire 5320, however, example embodiments are not limited thereto. For example, the at least one conductive member attached to the first connector 5100 may be a conductive paint or metal applied to a pliable material, thus, at least one conductive member 5300 connected to the first connector 5100 is not required to be a wire or a plurality of wires. For at least the same reasons, the at least one conductive member 5400 connected to the second connector 5200 is not required to be a plurality of wires.

Figure 33:
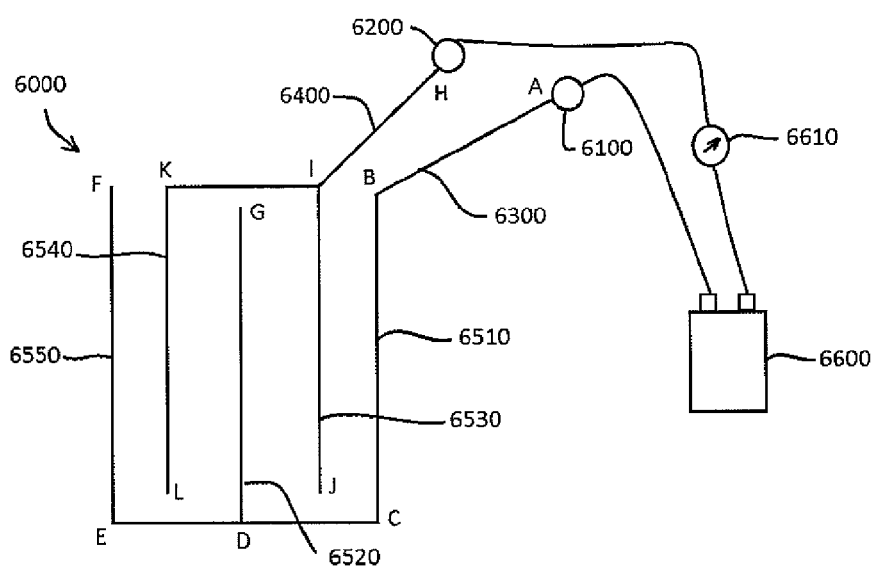
FIG. 33 is a view of a fluid detection device in accordance with example embodiments.

FIG. 33 is another example of a sensor system 6000 in accordance with example embodiments. As shown in FIG. 33, the sensor system 6000 may include a first connector 6100, a second connector 6200, a voltage source 6600, and a detector 6610 which may be configured to detect a current flowing through the sensor system 6000. In example embodiments, the first connector 6100 and the second connector 6200 may be, but are not limited to, snaps, clips, or buttons. In example embodiments, the voltage source 6600 may be, but is not limited to, a battery or a wall socket connected to AC power. In example embodiments the detector 6610 may be, but is not limited to, a current detector such as an ammeter.

In example embodiments, the sensor system 6000 may include at least one conductive member 6300 connected to first connector 6100 and at least one conductive member 6400 connected to the second connector 6200. The at least one conductive member 6300 attached to the first connector 6100, for example, may be a wire with a bifurcated end and the at least one conductive member 6400 attached to the second connector 6200 may be a wire with a bifurcated end. For example, as shown in FIG. 33, the at least one conductive member 6300 may be a single wire. Along points A, B, C, and D, the single wire may be substantially intact. However, at point D the wire may split to have a bifurcated end having endpoints at points F and G. Similarly, as shown in FIG. 33, the at least one conductive member 6400 may be a single wire. Along points H to I the single wire may be substantially intact. However, at point I the wire may split to have a bifurcated end having endpoints at points L and J As shown in FIG. 33, the sensor system 6000 may include a sensing area comprised of a first leg 6510, a second leg 6520, a third leg 6530, a fourth leg 6540 and a fifth leg 6550. The first leg 6510 may be comprised of the conductive member 6300. For example, as shown in FIG. 33, a portion of the conductive member 6300 extending from point B to point C may form the first leg 6510. The second leg 6520 may be comprised of one end of the bifurcated end of the conductive member 6300 extending from point D to point G. The fifth leg 6550 may be comprised of the other end of the bifurcated end of the conductive member 6300 extending from point E to point F. In example embodiments, the portion of the bifurcated end of the conductive member 6400 extending from point I to J may form the third leg 6530 whereas the other portion of the bifurcated end of the conductive member 6400 extending from point K to point L may form the fourth leg 6540. Thus, the sensing area may be comprised of a first plurality of legs (6510, 6520, and 6550) and a second plurality of legs (6530 and 6540) which are alternatively arranged. Furthermore, the first plurality of legs (6510, 6520, and 6550) may be formed by a single wire with a bifurcated end and the second plurality of legs may likewise be formed of a single wire with a bifurcated end.

In example embodiments, each of the first, second, third, fourth, and fifth legs 6510, 6520, 6530, 6540, and 6550 may be substantially parallel to each other and may be spaced about 1 cm apart from one another. Example embodiments, however, are not limited thereto as first, second, third, fourth, and fifth legs 6510, 6520, 6530, 6540, and 6550 are not required to be parallel with one another. Furthermore, the first, second, third, fourth, and fifth legs 6510, 6520, 6530, 6540, and 6550 may be spaced closer together than about 1 cm or farther apart than about 1 cm.

In example embodiments the sensor systems 5000 and 6000 may be on, adhered to, or attached to a supporting member, for example, a garment (such as an undergarment) or a wrap. The supporting structure may be made of a pliable and fluid absorbable material such as muslin cloth, however, example embodiments are not limited thereto.

Figure 34:
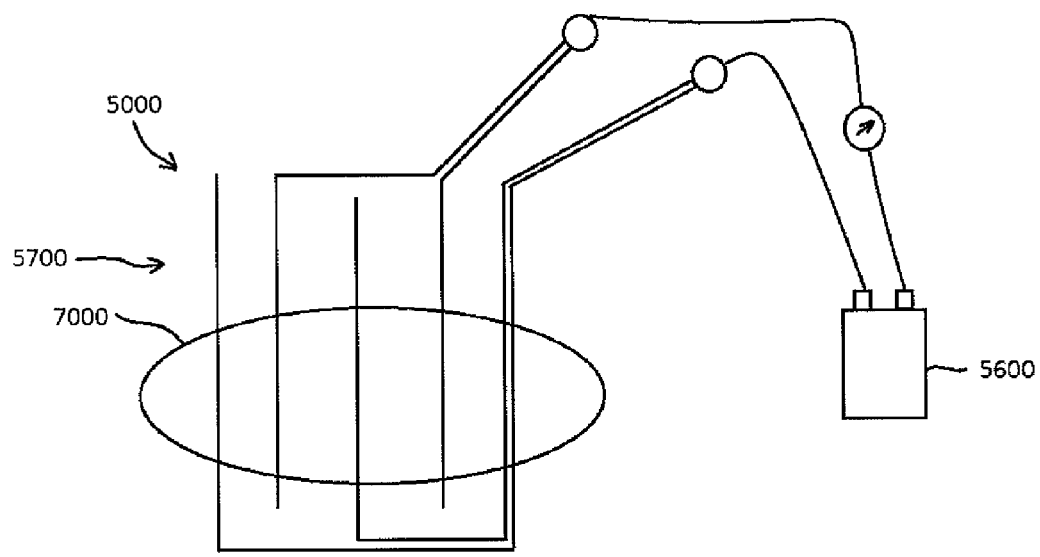
FIG. 34 is a view of a fluid detection device in accordance with example embodiments.
Figure 35:
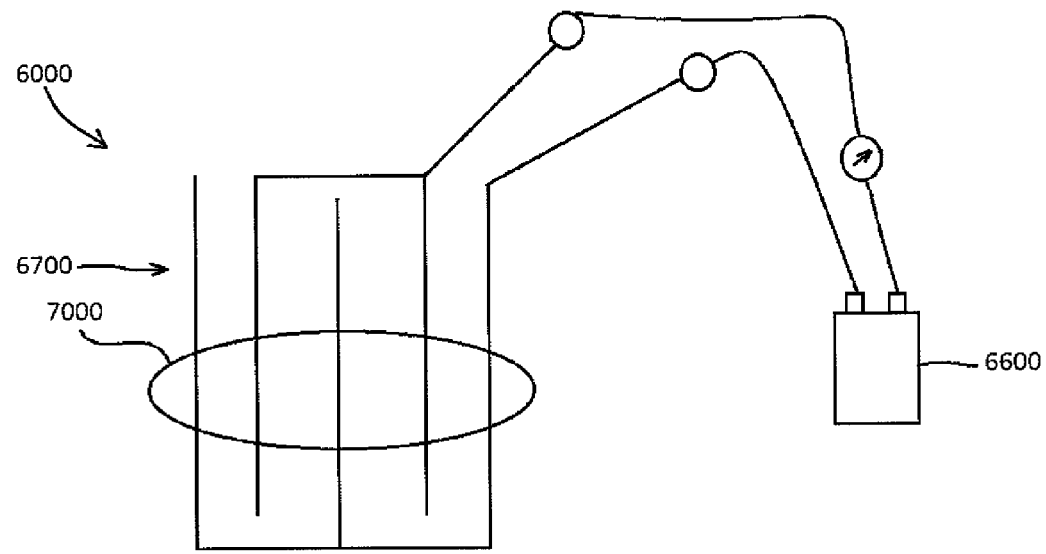
FIG. 35 is a view of a fluid detection device in accordance with example embodiments in which a fluid is contacting the fluid detection device.

FIGS. 34 and 35 illustrate the sensor systems 5000 and 6000 on the supporting structure. As shown in FIGS. 34 and 35, a voltage sources 5600 and 6600 are attached to the first and second connectors 5100, 6100 and 5200, 6200. In example embodiments, the voltage sources 5600 and 660 generate electric fields across the legs of the sensing areas of the sensor systems 5000 and 6000. However, because the first, second, and fifth legs 5510, 5520, 5550, 6510, 6520, and 6550 are not electrically connected to the third and fourth legs 5530, 5540, 6530, and 6540, current cannot flow through the circuit formed by the aforementioned legs. In other words, the sensors systems 5000 and 6000 behave as an open circuit in the absence of a condutive material or substance, for example, blood or urine. However, in the event the sensor systems 5000 and 6000 are exposed to a fluid 7000, for example, a body fluid such as blood or urine, the fluid may act as a conduit through which electricity may flow. Thus, in example embodiments, the sensing systems 5000 and 6000 may detect a fluid, for example, a body fluid, in a vicinity of the sensing areas by determining whether current is flowing through the sensing systems 5000 and 6000. In other words, when a fluid, for example, blood, urine, or a fluid which is capable of conducting electricity, is placed between the because the first, second, and fifth legs 5510, 5520, 5550, 6510, 6520, and 6550 and the third and fourth legs 5530, 5540, 6530, and 6540, the fluid acts as a conductor and sensing systems 5000 and 6000 then behave as a closed circuit.

In example embodiments, an alarm may be connected to the detectors 5610 and 6610. The alarm, for example, may be configured as an audible and/or visual alarm. In example embodiments, the alarm may be connected to the detectors 5610 and 6610 either by wires or by using a wireless technology. For example, the detectors 5610 and 6610 may include transmitters and the alarms may include receivers. In addition, rather than, or in addition to, sending signals to an alarm, the detectors 5610 and 6610 may send signals to a computer which may be part of a monitoring station.

Figure 36:
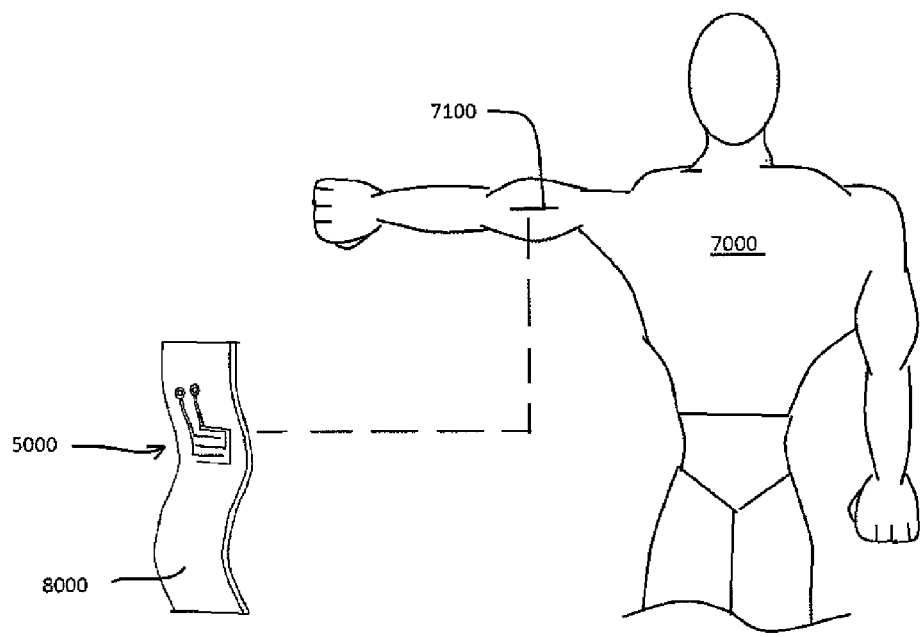
FIG. 36 is a view of a fluid detection device in accordance with example embodiments in which a fluid is contacting the fluid detection device.
Figure 37:
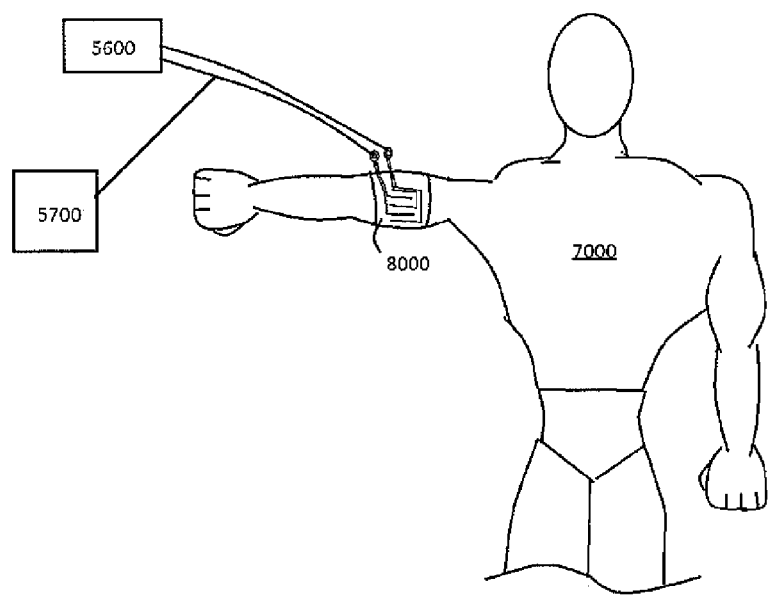
FIG. 37 is a view of a fluid detection device in accordance with example embodiments.

FIG. 36 is a view of the sensing system 5000 attached to a wrap 8000 in accordance with example embodiments. The wrap 8000 may, for example, be formed of a fluid absorbable material, for example, muslin cloth. In FIG. 36 a patient 7000 is illustrated having an incision 7100 in one arm. As shown in FIG. 37, the wrap 8000 may be placed around the patients arm such that the sensing system 5000 is near the vicinity of the incision 7100. In example embodiments, the first and second connectors of the sensing system may be attached to voltage source 5600 and a detector, for example, an ammeter, may be incorporated in the sensing system 5000 to determine whether current is flowing through the sensing system 5000. In the event blood leaks from the incision 7100 and through the wrap 8000, the blood may act as a conduit through which electrical current may pass. Thus, blood may be detected by the detector 5700 when current is determined to be flowing through the sensing system 5000.

Figure 38:
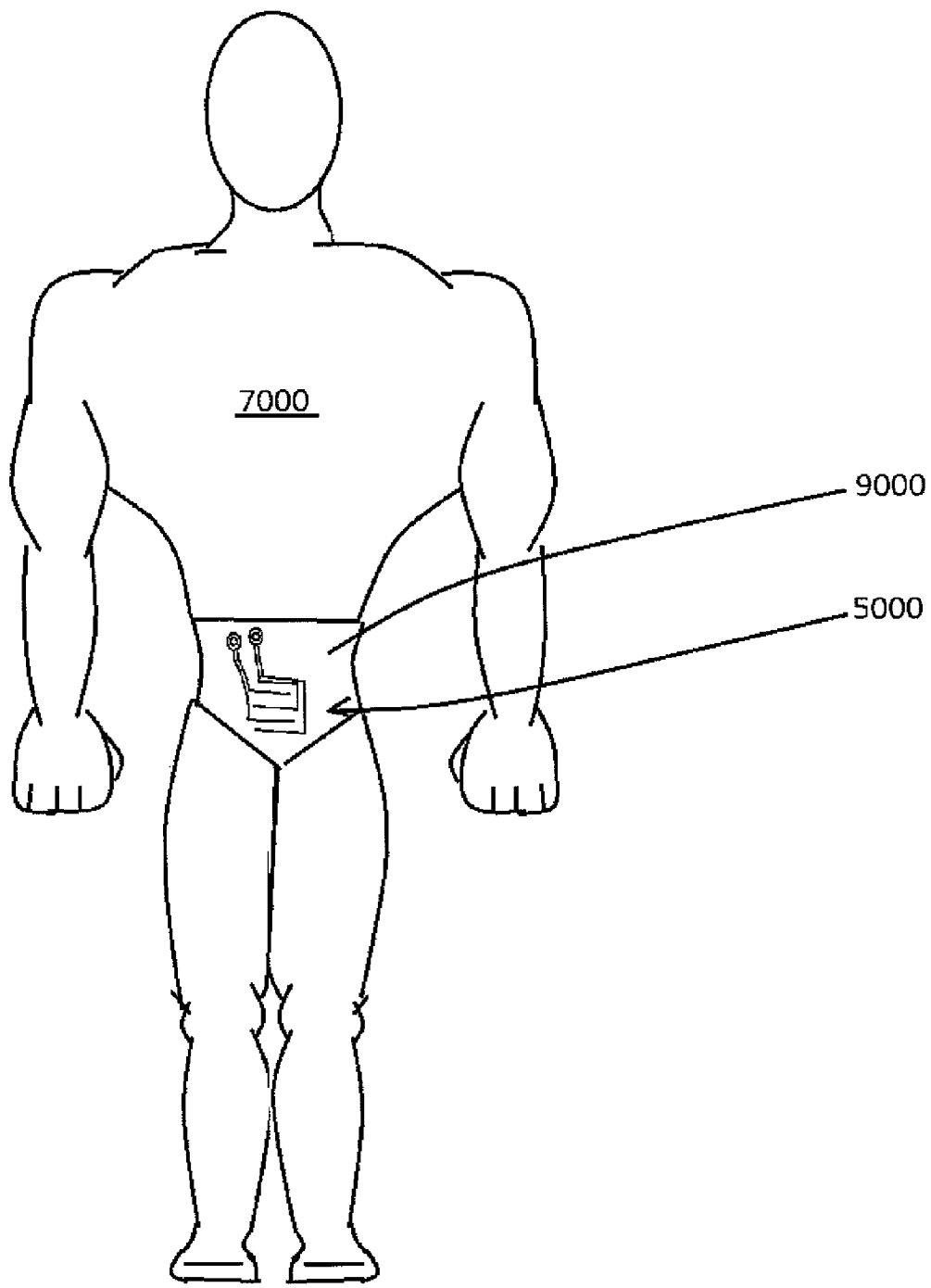
FIG. 38 is a view of a fluid detection device in accordance with example embodiments.

FIG. 38 illustrates the use of the sensing system 5000 incorporated in an undergarment 9000. In this particular non-limiting example, sensing system 5000 may be used to detect a bodily fluid, for example, urine. As described previously, urine may facilitate a transfer of current through the sensing system 5000. Thus, in example embodiments, the sensing system 5000 may be used to detect the presence of urine in a manner similar to that described above.

Example embodiments are directed to sensing systems which are capable of sensing a fluid. The fluid may be capable of facilitating a transfer of current through it. For example, the fluid may contain electrolytes, for example, sodium chloride or potassium chloride, that facilitate a current traveling through it. Nonlimiting examples of the fluid include bodily fluid. For example, the fluid may be, but is not limited to, blood and/or urine. Fluids that are poor conductors, for example, petroleum, are not considered usable with the sensing systems of example embodiments.

While example embodiments have been particularly shown and described with reference to example embodiments thereof, it will be understood by those of ordinary skill in the art that various changes in form and details may be made therein without departing from the spirit and scope of the invention.

We claim:

1. A sensor system comprising:
   a first connector;
   a second connector;
   a supporting member comprising a pliable and fluid absorbable material;
   at least one conductive member connected to the first connector, the at least one conductive member forming a first leg and a second leg; and
   at least one conductive member connected to the second connector, the at least one conductive member connected to the second connector forming a third leg between the first leg and the second leg, wherein
      the at least one conductive member connected to the first connector and the at least one conductive member connected to the second connector are on the supporting member,
      the at least one conductive member connected to the second connector forms a fourth leg such that the second leg is between the third leg and the fourth leg,
      the at least one conductive member connected to the first connector forms a fifth leg such that the fourth leg is between the fifth leg and the second leg,
      the at least one conductive member connected to the first connector is comprised of a first electrically conductive wire and a second electrically conductive wire, at least a portion of the first and second electrically conductive wires being substantially parallel and arranged adjacent one another to form the first leg, the first electrically conductive wire forming the second leg, and the second electrically conductive wire forming the fifth leg,
      the at least one conductive member connected to the second connector is comprised of a third electrically conductive wire and a fourth electrically conductive wire, the third electrically conductive wire forming the third leg, and the electrically conductive fourth wire forming the fourth leg,
      the first and second electrically conductive wires being separately connected to the first connector and the second and third electrically conductive wires are separately connected to the second connector.

2. The sensor system according to claim 1, wherein the first connector and the second connector are connected to a voltage source.

\* \* \* \* \*